US010073077B2

(12) United States Patent
Matsuura et al.

(10) Patent No.: US 10,073,077 B2
(45) Date of Patent: Sep. 11, 2018

(54) METHOD FOR INVESTIGATION OF LIVER DAMAGE TYPE

(71) Applicant: Daiichi Sankyo Company, Limited, Tokyo (JP)

(72) Inventors: Tomokazu Matsuura, Tokyo (JP); Katsushi Amano, Tokyo (JP); Tomonori Sugita, Tokyo (JP); Noriko Masubuchi, Tokyo (JP); Masahiro Sugihara, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 113 days.

(21) Appl. No.: 14/907,828

(22) PCT Filed: Aug. 4, 2014

(86) PCT No.: PCT/JP2014/070426
§ 371 (c)(1),
(2) Date: Jan. 27, 2016

(87) PCT Pub. No.: WO2015/019976
PCT Pub. Date: Feb. 12, 2015

(65) Prior Publication Data
US 2016/0169862 A1    Jun. 16, 2016

(30) Foreign Application Priority Data

Aug. 5, 2013    (JP) ................................ 2013-162429

(51) Int. Cl.
| | |
|---|---|
| *G01N 33/52* | (2006.01) |
| *G01N 33/487* | (2006.01) |
| *G01N 33/50* | (2006.01) |
| *G01N 33/53* | (2006.01) |
| *H01J 49/00* | (2006.01) |

(52) U.S. Cl.
CPC .......... *G01N 33/487* (2013.01); *G01N 33/50* (2013.01); *G01N 33/5308* (2013.01); *H01J 49/0036* (2013.01); *G01N 2400/40* (2013.01); *G01N 2800/085* (2013.01); *G01N 2800/52* (2013.01)

(58) Field of Classification Search
None
See application file for complete search history.

(56) References Cited

U.S. PATENT DOCUMENTS

| 6,060,255 A | 5/2000 | Shibuya et al. | |
|---|---|---|---|
| 2003/0119064 A1* | 6/2003 | Valkirs .................. | G01N 33/573 435/7.1 |
| 2011/0098192 A1 | 4/2011 | Lo et al. | |

FOREIGN PATENT DOCUMENTS

| CA | 2078588 A1 | 3/1993 |
|---|---|---|
| JP | S56-126744 A | 10/1981 |
| JP | 2012-002610 A | 1/2012 |

OTHER PUBLICATIONS

Festi et al., Diagnostic Effectiveness of Serum Bile Acids in Liver Diseases as Evaluated by Multivariate Statistical Methods, Hepatology, vol. 3, No. 5, 1983, pp. 707-713. (Year: 1983).*
Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Guicciardi et al., Cholestatic hepatocellular injury: what do we know and how should we proceed, Journal of Hepatology 42, 2005, pp. 297-300. (Year: 2005).*
Search Report issued in corresponding European Patent Application No. 14 834 659.6 dated Feb. 10, 2017 (8 pages).
Office Action issued in corresponding Chinese Patent Application No. 2014800440334 dated Jun. 11, 2017 (English translation) (4 pages).
Castano et al., "Bile acid profiles by capillary electrophoresis in intrahepatic cholestasis of pregnancy," Clinical Science, (2006), vol. 110, No. 4, pp. 459-465.
Fujiwara, K., "Clinical Examination of Serum Bile Acids for the Diagnosis of Hepatobiliary Diseases," Jpn J Clin Pathol, vol. 37, (1989), pp. 1114-1121 (with English translation) (12 pages).
Iwamura, K., "Changes of Plasma Bile Acid Levels and Their Clinical Significance in Drug-Induced Liver Injury," Tokai J Exp Clin Med., vol. 9, No. 2, 1984, pp. 109-117.
Masubuchi et al., "Oxidative stress markers, secondary bile acids and sulfated bile acids classify the clinical liver injury type: Promising diagnostic biomarkers for colestasis," Chemico-Biological Interactions, vol. 255 (2016), pp. 83-91.
Sugiyama et al., "Clinical Evaluation of Serum 3beta-Hydroxy-5-Cholenoic Acid in Hepatobiliary Diseases," Gastroenterologia Japonica, vol. 21, No. 6, 1986, pp. 608-616.
Manual for handling disorders due to adverse drug reactions, Drug-induced liver injury: 10-30 (Apr. 2008, Ministry of Health, Labour and Welfare) (107 pages).

(Continued)

*Primary Examiner* — Gary Counts
(74) *Attorney, Agent, or Firm* — Kilyk & Bowersox, P.L.L.C.

(57) ABSTRACT

Provided is a test method for discriminating a liver injury type using as an indicator a level of lithocholic acid (hereinafter abbreviated as LCA) in a biological sample of a subject. That is, provided is a test method comprising measuring a level of LCA in a biological sample collected from a subject, and discriminating a liver injury type as hepatocellular injury type, cholestasis type, or a mixed type thereof using the measured level of LCA as an indicator.

19 Claims, 2 Drawing Sheets

(56) References Cited

OTHER PUBLICATIONS

Bouchier et al., "Serum bile acids in hepatobiliary disease," Gut, 1978, vol. 19, pp. 492-496.
Fischer et al., "Hepatic levels of bile acids in end-stage chronic cholestatic liver disease," Clinica Chimica Acta, vol. 251, 1996, pp. 173-186.
Williams, C.N., "Bile-Acid Metabolism and the Liver," Clin. Biochem., 9, (3), 1976, pp. 149-152.
Berr et al., "Disorders of Bile Acid Metabolism in Cholesterol Gallstone Disease," J. Clin. Invest., vol. 90, 1992, pp. 859-868.
Ostrow, J.D., "Metabolism of Bile Salts in Cholestasis in Humans," Hepatic Transport and Bile Secretion: Physiology and Pathophysiology, N. Tavoloni and P.D. Berk (Eds), Raven Press, New York, 1993, pp. 673-712.
Burkard et al., "Differentiated quantification of human bile acids in serum by high-performance liquid chromatography-tandem mass spectrometry," Journal of Chromatography B, vol. 826, 2005, pp. 147-159.
Palmeira et al., "Mitochondrially-mediated toxicity of bile acids," Toxicology, vol. 203, 2004, pp. 1-15.
Danan et al., "Causality Assessment of Adverse Reactions to Drugs—I. A Novel Method Based On the Conclusions of International Consensus Meetings: Application to Drug-Induced Liver Injuries," J Clin Epidemiol, vol. 46, No. 11, 1993, pp. 1323-1330.
Takigawa, et al., "Proposal for DDW-J 2004 Workshop Diagnostic Criteria for Drug-induced Liver Injury," Kanzo, 46 (2), 2005, pp. 85-90 (17 pages).
Masubuchi et al., "Promising Toxicological Biomarkers for Diagnosis of Liver Injury Types: Bile Acid Metabolic Profiles As Screening Tool in Drug Development," 24th Annual Meeting of the Japanese Society for the Study of Xenobiotics, 2009, p. 305 (one page).
Stiehl, A., "Bile Salt Sulphates in Cholestasis," European Journal of Clinical Investigation, vol. 4, 1974, pp. 59-63.
International Search Report issued in corresponding International Patent Application No. PCT/JP2014/070426 dated Nov. 11, 2014 (7 pages).
Nakamura et al., "Advancement of Basic and Clinical Research in Pathophysiology. Cholestasis and Cholestatic Factors," Journal of Clinical and Experimental Medicine, 1999, pp. 12-14 (9 pages).
Lucangioli et al., "Lithocholic acid as a biomarker of intrahepatic cholestasis of pregnancy during ursodeoxycholic acid treatment," Annals of Clinical Biochemistry, 2009, vol. 46, pp. 44-49.
Kimura, T., "Study on Hepatotoxicity of Bile Acids," Japanese Journal of Gastroenterology, 1980, vol. 77, No. 2, pp. 185-194 (27 pages).

\* cited by examiner

METHOD FOR INVESTIGATION OF LIVER DAMAGE TYPE

The present application is a National Stage Application of PCT/JP2014/070426, filed Aug. 4, 2014, which claims priority to Japanese Patent Application No. 2013-162429, filed Aug. 5, 2013.

TECHNICAL FIELD

The present invention relates to a test method for liver injury, and more particularly, to a test method for discriminating a liver injury type. More particularly, the present invention relates to a test method comprising measuring a level of lithocholic acid (hereinafter sometimes abbreviated as LCA) in a biological sample collected from a subject, and discriminating a liver injury type using the measured level of LCA as an indicator.

BACKGROUND ART

Liver is a glandular tissue connected to digestive tract and has various important functions for living organisms, such as production and secretion of bile, a detoxification action, carbohydrate metabolism, protein metabolism, production of a blood coagulation factor, a hormone regulation action, and storage of various components of living organisms, including fat, glycogen, a protein, and a vitamin. Therefore, when those functions are acutely or chronically damaged due to viral infection, a drug or a toxic agent, or excess alcohol intake, the maintenance of homeostasis of liver functions is disrupted, resulting in a critical health problem. Among various diseases found in comprehensive medical examination or the like, liver dysfunction accounts for a high proportion of the diseases, and about 30% of Japanese adults are estimated to have liver dysfunction.

Diseases included in liver disorders are classified based on their etiologies or clinical symptoms. For example, the diseases may be classified based on their etiologies into viral hepatitis, drug-induced liver injury, alcoholic liver injury, autoimmune liver injury, metabolic liver injury, and the like. In addition, the diseases may be classified based on their clinical symptoms into hepatocellular injury type and cholestasis type. Hepatocellular injury is found in viral hepatitis, toxic liver injury, fatty liver, cirrhosis, and the like. Hepatocellular injury is caused by, for example, necrosis, fatty metamorphosis, multinucleation, or nuclear vacuolar degeneration of a hepatocyte. The hepatocyte, which is also referred to as hepatic parenchymal cell, is one of the cells constituting liver and accounts for most major parts of liver. The hepatocyte is an exocrine cell which secrets bile, while it is also an endocrine cell which secretes plasma proteins into an apical membrane side and stores glycogen to regulate blood glucose. Therefore, when the hepatocyte is damaged, a significant reduction in liver function is caused. Cholestasis is caused by blockade of bile excretion from liver due to some cause, with the result that abnormal excretion of bile is brought about over a part or whole of intrahepatic or extrahepatic bile duct system, and thereby the bile accumulates in liver and blood. Then, various symptoms such as jaundice and hepatitis are induced.

At present, diagnosis and treatment of liver diseases are performed according to an approach in which a physician empirically diagnoses a liver injury type using a symptom of a patient and values of serum biochemical parameters as indicators and then treatment is started (Non Patent Literature 1). Enzymes which leak from the hepatocyte by hepatocellular injury are used as the biochemical parameters. Specifically, there are used, for example, aspartate aminotransferase (hereinafter abbreviated as AST; sometimes referred to as glutamate-oxaloacetate transaminase (GOT)), alanine aminotransferase (hereinafter abbreviated as ALT; sometimes referred to as glutamate-pyruvate transaminase (GPT)), γ-glutamyl transpeptidase (hereinafter abbreviated as γ-GTP), and alkaline phosphatase (hereinafter abbreviated as ALP).

In addition, in non-clinical and clinical practices, measurement of total bile acids (hereinafter abbreviated as TBA) is generally performed. Bile acids is a general term for compounds that are steroid derivatives having cholanic acid skeletons widely found in bile of mammals and are major components of bile which plays a key role in digestion and absorption of fat. The bile acids are produced from metabolism of cholesterol in hepatocytes of liver (FIG. 1), followed by conjugating with glycine and taurine (aminoethylsulfonic acid) or the like, and then excreted as bile. The bile acids are roughly classified into primary bile acids and secondary bile acids. The primary bile acids are bile acids which are synthesized in liver. Examples of the primary bile acids may include cholic acid (hereinafter sometimes abbreviated as CA), chenodeoxycholic acid (hereinafter sometimes abbreviated as CDCA), and ursodeoxycholic acid (hereinafter sometimes abbreviated as UDCA) which has an isomeric relationship with CDCA. The secondary bile acids are bile acids which are produced from the primary bile acids excreted via bile duct to intestinal tract in a dehydroxylation reaction, a dehydrogenation reaction, a hydrogenation reaction, or a deconjugation reaction by enterobacteria. Examples of the secondary bile acids may include deoxycholic acid (hereinafter sometimes abbreviated as DCA) and LCA. Those five kinds of bile acid components given as examples each have three forms which are a free form, a glycine-conjugated form, and a taurine-conjugated form. In addition, some bile acid components each have a sulfated form or a glucuronidated form. In many animal species including humans, CA and CDCA having hydroxyl groups at position 3, 7, and 12 of a cholanic acid skeleton are produced as the primary bile acids. Meanwhile, some animals produce bile acids inherent in the species. For example, α-muricholic acid (hereinafter sometimes abbreviated as αMCA) and β-muricholic acid (hereinafter sometimes abbreviated as βMCA) are found in mice and hyocholic acid (hereinafter sometimes abbreviated as HCA) is found in swine, and these bile acids are rare in humans and are characteristic of each of the animal species. αMCA and βMCA are primary bile acids and taurine-conjugated forms thereof are also known. HCA is a primary bile acid and produces hyodeoxycholic acid (hereinafter abbreviated as HDCA) by its 7α-dehydroxylation in intestine. Those bile acid components also have glycine-conjugated forms and taurine-conjugated forms.

In treatment of liver diseases, discrimination of a liver injury type is important for selection of treatment suitable for each liver injury type. Hitherto, liver injury types have been determined based on biochemical parameters. For example, a liver injury type is determined using, as indicators, increases in ALT and AST in hepatocellular injury type and increases in ALP and γ-GTP in cholestasis type. However, a determination method based on biochemical parameters sometimes leads to misjudgment of a liver injury type. Therefore, an attempt has been made to measure levels of many components constituting bile acids in serum and discriminate a liver injury type based on the results to further determine a therapeutic strategy.

There have been previous reports on various relationships between classification of liver injury types based on etiologies and levels of bile acid components (Non Patent Literatures 2 to 6). However, no consensus has been reached and no clinical application has been achieved.

In addition, there have been some reports on the association between classification of liver injury types based on clinical symptoms and levels of bile acid components (Non Patent Literatures 6 to 8). However, similarly to the classification of liver injury types based on etiologies, a variety of results have been shown and no consensus has been reached. Meanwhile, for classification of types of drug-induced liver injury based on clinical symptoms, there has been proposed an assessment method using biochemical parameters rather than bile acid components (Non Patent Literature 9). Based on this proposal, the Japan Society of Hepatology either proposes scoring of drug-induced liver injury (Non Patent Literature 10). Further, the inventors of the present invention have reported that a liver disease caused by administration of a drug to a rat was compared to a typical cholestasis model obtained by ligation of bile duct, or administration of 1-naphtyl isothiocyanate (ANIT), or the like, and that injury types of liver diseases may be discriminated by measuring levels of bile acid components (Non Patent Literature 11). However, at present, there is no report on a definitive biomarker that clinically diagnoses an early stage of cholestasis in liver at a capillary bile duct level. Thus, the decision of a therapeutic strategy is difficult in many cases.

CITATION LIST

Non Patent Literature

[NPL 1] Manual for handling disorders due to adverse drug reactions, Drug-induced liver injury: 10-30 (April 2008, Ministry of Health, Labour and Welfare).
[NPL 2] I A Bouchier, C R Pennington, Serum bile acids in hepatobiliary disease. Gut. June; 19(6):492-6 (1978).
[NPL 3] Fischer, S, Beuers, U, Spengler, U, Zwiebel, F M, Koebe, H-G, Hepatic levels of bile acids in end-stage chronic cholestatic liver disease. Clinica Chimica Acta. 251(2):173-86 (1993).
[NPL 4] Williams C N, Bile-acid metabolism and the liver. Clin Biochem. 9(3):149-52 (1976).
[NPL 5] Berr F, Pratschke E, Fischer S, Paumgartner G. Disorders of bile acid metabolism in cholesterol gallstone disease. J Clin Invest. 90(3):859-68 (1992).
[NPL 6] Ostrow J D, Metabolism of bile salts in cholestasis in humans. In: Tavoloni, N, Berk, P D (Eds), Hepatic transport and bile secretion. Raven, N.Y., pp. 673-712 (1993).
[NPL 7] Burkard I, von Eckardstein A, Rentsch K M, Differentiated quantification of human bile acids in serum by high-performance liquid chromatography-tandem mass spectrometry. J Chromatogr B Analyt Technol Biomed Life Sci. 826 (1-2):147-59 (2005).
[NPL 8] Palmeira C M, Rolo A P, Mitochondrially-mediated toxicity of bile acids. Toxicology. 203(1-3):1-15 (2004).
[NPL 9] Danan G, Benichou C. Causality assessment of adverse reactions to drugs-I. A novel method based on the conclusions of international consensus meetings: application to drug-induced liver injuries. J Clin Epidemiol. 46(11):1323-30 (1993).
[NPL 10] Hajime Takigawa, Proposal of diagnostic criteria of drug induced hepatic injury in DDW-J2004 workshop, Kanzo, 46(2):85-90 (2005).
[NPL 11] Noriko Masubuchi et al., 24th Annual Meeting of The Japanese Society for the Study of Xenobiotics, p. 305, 2-P-43, 2009.
[NPL 12] A. Stiehl, Bile Salt Sulphatesin Cholestasis. European Journal of Clinical Investigation. 4 (1):59-63 (1974).

SUMMARY OF INVENTION

Technical Problem to be Solved by the Invention

Liver injuries can be classified into hepatocellular injury type and cholestasis type based on clinical symptoms. There is no established technique capable of determining those types, although discrimination of the types is important for selection of treatment suitable for each of the types. Therefore, treatment such as medication is currently performed according to a physicians' comprehensive decision based on their clinical experience during common treatment. Hitherto, in the case of determining a liver injury type based on a biochemical parameter, increased ALT and AST have been used as an indicator of hepatocellular injury type, while increased ALP and γ-GTP have been used as an indicator of cholestasis type. However, determination based on only those indicators leads to misjudgment in some cases. Accordingly, a marker capable of more definitely discriminating a liver injury type at the initial stage of the onset of the liver disease enables early determination of a therapeutic strategy.

An object of the present invention is to find a useful biomarker which enables early diagnosis of a liver injury type, and provide a method of discriminating a liver injury type or a method of assisting discrimination of a liver injury type, in both of which the biomarker is used as an indicator.

Solution to Problem

The inventors of the present invention have made intensive investigations to achieve the object, and found the association of a level of lithocholic acid with a liver injury type by measuring levels of 24 kinds of bile acid components, a hepatic fibrosis marker, and an oxidative stress marker in clinical serum samples and subjecting the data obtained by the measurement to multivariable analysis. Specifically, the level of lithocholic acid showed a tendency to be high in hepatocellular injury-type liver injury in a population of patients with liver injury, and in contrast, the level showed a tendency to be low in cholestasis-type liver injury. In addition, it is found that in hepatocellular injury-type liver injury, a level of ursodeoxycholic acid showed a tendency to be low and a level of type IV collagen, which was a hepatic fibrosis marker, showed a tendency to be high. Meanwhile, in cholestasis-type liver injury, a level of deoxycholic acid showed a tendency to be low, and levels of serum sulfated bile acid (hereinafter abbreviated as SSBA), type IV collagen and hyaluronic acid (hereinafter abbreviated as HA), which were hepatic fibrosis markers, and reactive oxygen species (hereinafter abbreviated as ROS), which was an oxidative stress marker, showed a tendency to be high. Further, levels of taurine conjugates and glycine conjugates of various bile acids showed similar tendencies to levels of the components in a free form. Thus, the inventors of the present invention have revealed that a liver injury type can be discriminated by using a biomarker including those bile acid components that show characteristic tendencies depending on liver injury types, and achieved the present invention.

That is, the present invention relates to the following.

1. A test method for discriminating a liver injury type, comprising measuring a level of LCA in a biological sample collected from a subject to use the level of LCA as an indicator.

2. The test method according to the above-mentioned item 1., further comprising comparing the measured level of LCA to a predetermined cut-off value of the level of LCA.

3. The test method according to the above-mentioned item 1., further comprising determining the liver injury type as hepatocellular injury type when the measured level of LCA is equal to or higher than a predetermined cut-off value of the level of LCA for identifying hepatocellular injury-type liver injury.

4. The test method according to the above-mentioned item 1., further comprising determining the liver injury type as cholestasis type when the measured level of LCA is equal to or lower than a predetermined cut-off value of the level of LCA for identifying cholestasis-type liver injury.

5. The test method according to the above-mentioned item 1., further comprising determining the liver injury type as a mixed type of hepatocellular injury type and cholestasis type when the measured level of LCA is higher than a predetermined cut-off value of the level of LCA for identifying hepatocellular injury-type liver injury and is lower than a predetermined cut-off value of the level of LCA for identifying cholestasis-type liver injury.

6. The test method according to the above-mentioned item 1., further comprising:

measuring any one or both of levels of UDCA and type IV collagen, to use as indicators the any one or both of levels of UDCA and type IV collagen in addition to the level of LCA; and determining the liver injury type as hepatocellular injury type when the measured level of LCA is equal to or higher than a predetermined cut-off value of the level of LCA for identifying hepatocellular injury-type liver injury and the measured level of UDCA and/or type IV collagen satisfies any one of the following:

(1) the level of UDCA is equal to or lower than a predetermined cut-off value of the level of UDCA for identifying hepatocellular injury-type liver injury;

(2) the level of type IV collagen is equal to or higher than a predetermined cut-off value of the level of type IV collagen for identifying hepatocellular injury-type liver injury; and (3) the level of UDCA is equal to or lower than a predetermined cut-off value of the level of UDCA for identifying hepatocellular injury-type liver injury and the level of type IV collagen is equal to or higher than a predetermined cut-off value of the level of type IV collagen for identifying hepatocellular injury-type liver injury.

7. The test method according to the above-mentioned item 1., further comprising:

measuring any one or more of levels of DCA, SSBA, type IV collagen, HA, and ROS, to use as indicators the levels of DCA, SSBA, type IV collagen, HA, and ROS in addition to the level of LCA; and determining the liver injury type as cholestasis type when the measured level of LCA is equal to or lower than a predetermined cut-off value of the level of LCA for identifying cholestasis-type liver injury and the measured levels of DCA, SSBA, type IV collagen, HA, and ROS satisfy any one or two or more of the following:

(4) the level of DCA is equal to or lower than a predetermined cut-off value of the level of DCA for identifying cholestasis-type liver injury;

(5) the level of SSBA is equal to or higher than a predetermined cut-off value of the level of SSBA for identifying cholestasis-type liver injury;

(6) the level of type IV collagen is equal to or higher than a predetermined cut-off value of the level of type IV collagen for identifying cholestasis-type liver injury;

(7) the level of HA is equal to or higher than a predetermined cut-off value of the level of HA for identifying cholestasis-type liver injury; and (8) the level of ROS is equal to or higher than a predetermined cut-off value of the level of ROS for identifying cholestasis-type liver injury.

8. The test method according to the above-mentioned item 1., further comprising:

measuring a level of type IV collagen, to use as an indicator the level of type IV collagen in addition to the level of LCA; and determining the liver injury type as a mixed type of hepatocellular injury type and cholestasis type when the measured level of LCA is higher than a predetermined cut-off value of the level of LCA for identifying hepatocellular injury-type liver injury and is lower than a predetermined cut-off value of the level of LCA for identifying cholestasis-type liver injury and when the measured level of type IV collagen is equal to or higher than a predetermined cut-off value of the level of type IV collagen for identifying cholestasis-type liver injury.

9. The test method according to the above-mentioned item 2., in which the predetermined cut-off value of the level of LCA is calculated from a receiver operating characteristic curve, which is hereinafter referred to as ROC curve, of the level of LCA.

10. The test method according to the above-mentioned item 3., 5., 6., or 8., in which the predetermined cut-off value of the level of LCA for identifying hepatocellular injury-type liver injury is calculated from a predetermined ROC curve of the level of LCA for hepatocellular injury-type liver injury.

11. The test method according to the above-mentioned item 4., 5., 6., or 8., in which the predetermined cut-off value of the level of LCA for identifying cholestasis-type liver injury is calculated from a predetermined ROC curve of the level of LCA for cholestasis-type liver injury.

12. The test method according to the above-mentioned item 6., in which the predetermined cut-off value of the level of LCA for identifying hepatocellular injury-type liver injury, the predetermined cut-off value of the level of UDCA for identifying hepatocellular injury-type liver injury, and the predetermined cut-off value of the level of type IV collagen for identifying hepatocellular injury-type liver injury are calculated from a predetermined ROC of the level of LCA for hepatocellular injury-type liver injury, a predetermined ROC of the level of UDCA for hepatocellular injury-type liver injury, and a predetermined ROC of the level of type IV collagen for hepatocellular injury-type liver disease, respectively.

13. The test method according to the above-mentioned item 7., in which the predetermined cut-off value of the level of LCA for identifying cholestasis-type liver injury, the predetermined cut-off value of the level of DCA for identifying cholestasis-type liver injury, the predetermined cut-off value of the level of SSBA for identifying cholestasis-type liver injury, the predetermined cut-off value of the level of type IV collagen for identifying cholestasis-type liver injury, the predetermined cut-off value of the level of HA for identifying cholestasis-type liver injury, and the predetermined cut-off value of the level of ROS for identifying cholestasis-type liver injury are calculated from a predetermined ROC of the level of LCA for cholestasis-type liver injury, a predetermined ROC of the level of DCA for cholestasis-type liver injury, a predetermined ROC of the level of SSBA for cholestasis-type liver injury, a predetermined ROC of the level of type IV collagen for cholestasis-type liver injury, a predetermined ROC of the level of HA for cholestasis-type liver injury, and a predetermined ROC of the level of ROS for cholestasis-type liver injury, respectively.
14. The test method according to any one of the above-mentioned items 1. to 13., in which the biological sample is a blood sample.
15. The test method according to any one of the above-mentioned items 1. to 14., in which the biological sample is a serum sample.
16. A selection method of a therapeutic agent for liver injury according to a liver injury type, wherein the method is applied for a subject whose liver injury type is determined by the test method of any one of the above-mentioned items 1 to 15.

Advantageous Effects of Invention

According to the present invention, the test method comprising measuring a level of LCA in a biological sample collected from a subject and discriminating a liver injury type using the measured level of LCA as an indicator can be provided.

The test method according to the present invention is used alone or in combination with measurement of biochemical parameters which has hitherto been performed, and thereby enables early diagnosis of liver injury types based on clinical symptoms, specifically, hepatocellular injury type, cholestasis type, and a mixed type thereof, and early determination of a therapeutic strategy. The test method according to t the present invention can be used in an examination for liver disease and is extremely useful as a method of assisting diagnosis and treatment of liver disease.

DESCRIPTION OF EMBODIMENTS

Figure 1:
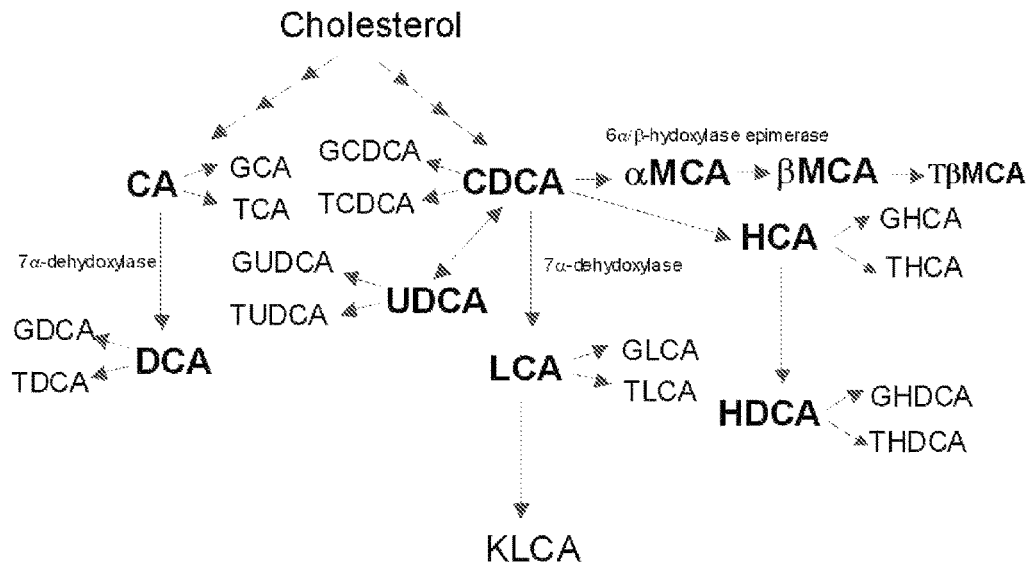
FIG. 1 is a view for illustrating a metabolic pathway of bile acids.

Abbreviations of bile acid components used in this description are shown in Table 1. In this description, the names of bile acid components are sometimes described as abbreviations shown in Table 1.

TABLE 1

| Bile acid components | Abbreviations |
|---|---|
| Cholic acid | CA |
| Glycocholic acid | GCA |
| Taurocholic acid | TCA |
| Deoxycholic acid | DCA |
| Glycodeoxycholic acid | GDCA |
| Taurodeoxycholic acid | TDCA |
| Chenodeoxycholic acid | CDCA |
| Glycochenodeoxycholic acid | GCDCA |
| Taurochenodeoxycholic acid | TCDCA |
| Ursodeoxycholic acid | UDCA |
| Glycoursodeoxycholic acid | GUDCA |
| Tauroursodeoxycholic acid | TUDCA |
| Lithocholic acid | LCA |
| Glycolithocholic acid | GLCA |
| Taurolithocholic acid | TLCA |
| 12-Ketolithocholic acid | 12_KLCA |
| α-Muricholic acid | αMCA |
| β-Muricholic acid | βMCA |
| Tauro-β-muricholic acid | TβMCA |
| Hyocholic acid | HCA |
| Glycohyocholic acid | GHCA |
| Taurohyocholic acid | THCA |
| Hyodeoxycholic acid | HDCA |

The present invention relates to a test method for liver injury, and more particularly, to a test method for discriminating a liver injury type. The test method according to the present invention comprises measuring a level of LCA in a biological sample collected from a subject, and discriminating a liver injury type using the measured level of LCA as an indicator. The discrimination of a liver injury type using the level of LCA as an indicator may be performed by comparing the measured level of LCA to a predetermined cut-off value of the level of LCA. An example of the test method according to the present invention may be a test method for discriminating a liver injury type, comprising measuring a level of LCA in a biological sample collected from a subject, and further comprising comparing the measured level of LCA to a predetermined cut-off value of the level of LCA.

In the test method according to the present invention, a level of a different biomarker from LCA, the biomarker being associated with a liver injury type, may be measured in addition to the level of LCA, and the liver injury type can be discriminated using the level of LCA and the level of the biomarker as indicators.

Examples of the different biomarker from LCA, the biomarker being associated with a liver injury type, may include UDCA and type IV collagen, which are associated with hepatocellular injury-type liver injury. In addition, as a biomarker associated with cholestasis-type liver injury, there may be given, for example, DCA, SSBA, type IV collagen, HA, and ROS.

The test method according to the present invention may be performed alone or in combination with various test methods, such as measurement of biochemical parameters, which have hitherto been performed.

The "liver injury type" as used herein means a type to be classified based on liver injury symptoms. The "liver injury symptoms" refer to various complaints and examination findings which are exhibited by a patient with liver injury. Specific examples of the "liver injury type" may include hepatocellular injury type and cholestasis type. In the hepatocellular injury type, a hepatic parenchymal cell, which is one of the cells constituting liver and accounts for most major parts of liver, is damaged, and a remarkable reduction in liver function is caused. The cholestasis type is caused by blockade of excretion of bile from liver due to some cause, with the result that abnormal excretion of bile is brought about over a part or whole of intrahepatic or extrahepatic bile duct system, and thereby the bile accumulates in liver and blood. Then, various symptoms such as jaundice and hepatitis are induced.

The test method according to the present invention can discriminate hepatocellular injury type and cholestasis type, and can also discriminate a type classified as both of the hepatocellular injury type and the cholestasis type, that is, a mixed type.

The "subject" to be subjected to the test method according to the present invention means an individual who has been diagnosed as having liver dysfunction and/or who is suspected of having liver dysfunction based on some testing results. The "subject" encompasses an individual who has a liver disease classified as viral hepatitis, drug-induced liver injury, alcoholic liver injury, autoimmune liver injury, metabolic liver injury, or the like or/and who is suspected as having the liver disease. Preferred is an individual who has been diagnosed as having liver dysfunction.

The "biological sample" as used herein is not particularly limited as long as the sample contains bile acid components, and a preferred example thereof may be a sample which may contain a hepatic fibrosis marker and/or an oxidative stress marker in addition to the bile acid components. Specific examples thereof may include blood isolated from a subject, and serum and plasma prepared from the blood, preferably serum.

A "therapeutic agent for liver injury" and a "treatment method of liver injury" as used herein include examples such as therapeutic agents for liver injury and treatment methods of liver injury which are described in "Manual for handling disorders due to adverse drug reactions, Drug-induced liver injury," and medications and treatment methods which are performed in medical facilities. In the case of the hepatocellular injury type, for example, intravenous injection of stronger Neo-Minophagen C formulation which is a glycyrrhizin formulation and has an anti-allergic action is performed as well as oral administration of UDCA having a hepatocyte membrane protecting action. When hepatocellular injury is increased in severity to induce fulminant hepatitis, for example, intravenous hyperalimentation (IVH) or artificial liver support is used. In the case of the cholestasis type, for example, vitamin A or vitamin K is administered for covering lack of a liposoluble vitamin and then UDCA, prednisolone, phenobarbital, taurine, colestimide, or the like is used as a medication.

LCA is one of the bile acids. The bile acids are produced from cholesterol metabolism in hepatocytes of liver, followed by conjugating with glycine and taurine (aminoethylsulfonic acid) or the like, and then excreted as bile, which play a key role in digestion and absorption of fat. LCA is a secondary bile acid produced in such a way that CDCA, which is one of the primary bile acids synthesized in liver, is excreted via bile duct into intestinal tract and subjected to a dehydration and oxidation reaction by 7-α dehydroxylase.

In a population of patients with liver injury, when levels of LCA in serum were compared between patients with hepatocellular injury-type liver injury and patients with cholestasis-type liver injury, the level of LCA showed a tendency to be high in the patients with hepatocellular injury-type liver injury, and in contrast, the level of LCA showed a tendency to be low in the patients with cholestasis-type liver injury. Further, in the cholestasis-type liver injury, a level of DCA in serum showed a tendency to be low and a level of SSBA showed a tendency to be high. Meanwhile, in the hepatocellular injury-type liver injury, a level of UDCA in serum showed a tendency to be low. Levels of taurine conjugates and glycine conjugates of various bile acids also showed a tendency to be similar to the levels of the components in a free form. It can be considered that: in the cholestasis-type liver injury, production of DCA and LCA is suppressed by cholestasis, which is accompanied by an increase in the levels of CA, CDCA, and UDCA; and in contrast, in the hepatocellular injury-type liver injury, production of DCA and LCA, which have high lipophilicity, is enhanced, resulting in suppression of production of CA, CDCA, and UDCA.

In the cholestasis-type liver injury, in addition to the level of LCA, levels of type IV collagen and HA, which are hepatic fibrosis markers, and ROS, which is an oxidative stress marker, in serum also showed a tendency to be high. Meanwhile, in the hepatocellular injury-type liver injury, the level of type IV collagen in serum showed a tendency to be high.

The discrimination of a liver injury type may be performed by comparing values of measurement items to their predetermined cut-off values. The "cut-off value" means a value which distinguishes between a positive range and a negative range. The cut-off values of measurement items may be individually set for liver injury types. The cut-off value may be set according to a method well known. For example, the cut-off value may be set using ROC analysis, which is generally used as a method of investigating usability of a diagnostic examination. In the ROC analysis, when shifting thresholds, an ROC curve is prepared which plots sensitivity for each threshold on the vertical axis and a false positive fraction (FPF, false-positive rate: 1-specificity) on the horizontal axis. In the case of the examination with no diagnostic capability, the ROC curve forms a diagonal straight line. Meanwhile, along with an improvement of a diagnostic capability of the examination, the diagonal line forms a curve which has an arc left-upward. In the case of the examination with a diagnosis capability of 100%, the diagonal line forms a curve which passes from a left side to an upper side. For the setting of the cut-off value, a method based on the fact that an ROC curve of independent variables having excellent sensitivity and specificity comes to near the upper left corner, is given as an example, in which a point having the minimum distance from the upper left corner is set as a cut-off value. Alternatively, a method may be given in which a point farthest from the diagonal dotted line at an area under the curve (abbreviated as AUC) of 0.500 in an ROC curve is set as a cut-off value, that is, (sensitivity+specificity-1) is calculated and a maximum point among the obtained values, i.e., Youden index may be set as the cut-off value. Herein, the "sensitivity" means a true positive rate. In addition, the "specificity" means a true negative rate. Besides, in an alternative method, the cut-off value may be quantitatively set based on the relationship between each of the measurement items and the frequency of a liver injury type.

Figure 2:
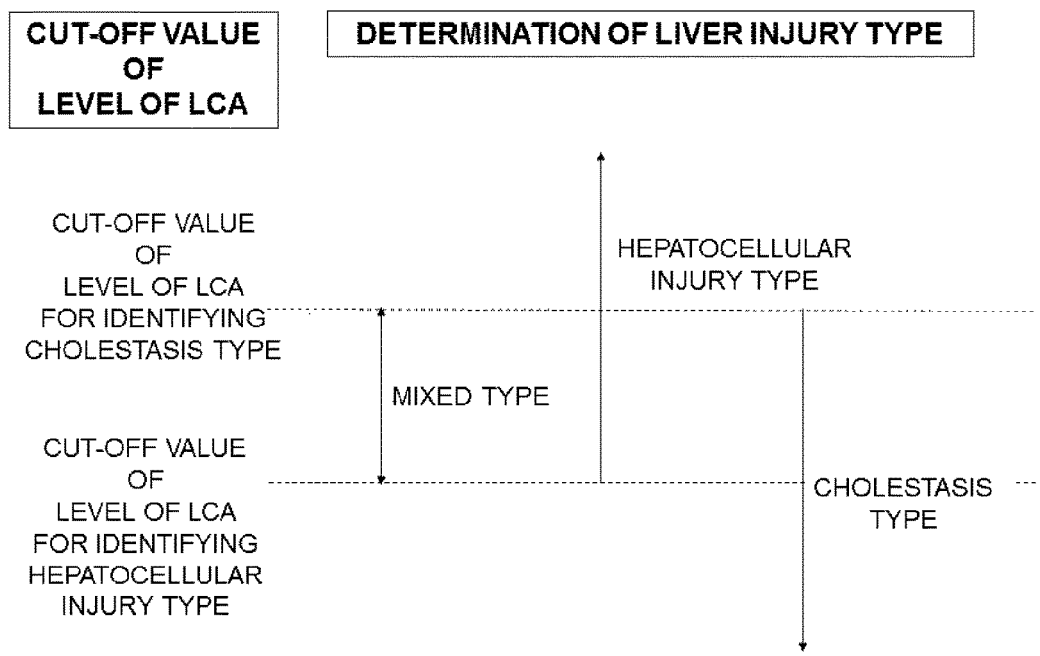
FIG. 2 is a view for illustrating a method of discriminating a liver injury type using a cut-off value of a level of LCA.

The discrimination of a liver injury type by the test method according to the present invention is described with referring to FIG. 2. When the level of LCA is equal to or higher than a predetermined cut-off value of the level of LCA for identifying hepatocellular injury-type liver injury, the liver injury type is determined as hepatocellular injury type. When the level of LCA is equal to or lower than a predetermined cut-off value of the level of LCA for identifying cholestasis-type liver injury, the liver injury type is determined as cholestasis type. In addition, when the level of LCA is higher than a predetermined cut-off value of the level of LCA for identifying hepatocellular injury-type liver injury and is lower than a predetermined cut-off value of the level of LCA for identifying cholestasis-type liver injury, the liver injury type is determined as a type containing both of hepatocellular injury-type and cholestasis type, that is, a mixed type. Further, for more detailed discrimination, when the level of LCA is higher than a predetermined cut-off value of the level of LCA for identifying cholestasis-type liver injury, the liver injury type is determined as hepatocellular injury type in which the mixed type is not included. In addition, when the level of LCA is lower than a predetermined cut-off value of the level of LCA for identifying hepatocellular injury-type liver injury, the liver injury type is determined as cholestasis type in which the mixed type is not included.

In the test method according to the present invention, any one or both of levels of UDCA and type IV collagen may be measured in addition to the level of LCA. The measured level of UDCA and/or type IV collagen is compared with the corresponding predetermined cut-off value. When the measured level of LCA is equal to or higher than a predetermined cut-off value of the level of LCA for identifying hepatocellular injury-type liver injury and the measured level of UDCA and/or type IV collagen satisfies any one of the following, the liver injury type can be determined as hepatocellular injury type: (1) the level of UDCA is equal to or lower than a predetermined cut-off value of the level of UDCA for identifying hepatocellular injury-type liver injury; (2) the level of type IV collagen is equal to or higher than a predetermined cut-off value of the level of type IV collagen for identifying hepatocellular injury-type liver injury; and (3) the level of UDCA is equal to or lower than a predetermined cut-off value of the level of UDCA for identifying hepatocellular injury-type liver injury and the level of type IV collagen is equal to or higher than a predetermined cut-off value of the level of type IV collagen for identifying hepatocellular injury-type liver injury.

In the test method according to the present invention, any one or more of levels of DCA, SSBA, type IV collagen, HA, and ROS may be measured in addition to the level of LCA. Each of the measured levels is compared with the corresponding predetermined cut-off value. When the measured level of LCA is equal to or lower than a predetermined cut-off value of the level of LCA and the measured levels of DCA, SSBA, type IV collagen, HA, and ROS satisfy any one or two or more of the following, the liver injury type can be determined as cholestasis type: (4) the level of DCA is equal to or lower than a predetermined cut-off value of the level of DCA; (5) the level of SSBA is equal to or higher than a predetermined cut-off value of the level of SSBA; (6) the level of type IV collagen is equal to or higher than a predetermined cut-off value of the level of type IV collagen; (7) the level of HA is equal to or higher than a predetermined cut-off value of the level of HA; and (8) the level of ROS is equal to or higher than a predetermined cut-off value of the level of ROS.

In the test method according to the present invention, a level of type IV collagen may be measured in addition to the level of LCA. The measured level is compared with the corresponding predetermined cut-off value. When the measured level of LCA is higher than a predetermined cut-off value of the level of LCA for identifying hepatocellular injury-type liver injury and is lower than a predetermined cut-off value of the level of LCA for identifying cholestasis-type liver injury and when the measured level of type IV collagen is equal to or higher than a predetermined cut-off value of the level of type IV collagen, the liver injury type can be determined as a mixed type of hepatocellular injury type and cholestasis type.

Specific examples of the cut-off values of the measurement items used in the test method according to the present invention are shown in Table 2-1 and Table 2-2. Table 2-1 shows specific examples of cut-off values of biomarkers for identifying hepatocellular injury-type liver injury. Table 2-2 shows specific examples of cut-off values of biomarkers for identifying cholestasis-type liver injury. Each of the cut-off values shown as examples is a cut-off value predetermined by measuring levels of biomarkers using as a biological sample a serum sample collected from a liver injury patient with no application of any therapeutic agent for liver injury, comparing the measured levels of biomarkers between a liver injury patient group and patients with hepatocellular injury-type liver injury or patients with cholestasis-type liver injury by ROC analysis, and determining a Youden index in Examples described below. The cut-off value may also be set for each measurement facility or population to be measured. The setting may be appropriately changed by storing measured data on a level of a biomarker of interest for the same samples as described above, and performing the analysis according to the same analytical approach as described above. In addition, when performing measurement of a level of a biomarker using a different sample from the serum sample, the cut-off value may be appropriately set according to the same analytical approach as described above by analyzing the measured data on each of levels of biomarkers from the sample to be used.

TABLE 2-1

| | | Cut-off values |
|---|---|---|
| Bile acid components | LCA (nmol/mL) | ≥0.01985 |
| | UDCA (nmol/mL) | ≤0.903 |
| Hepatic fibrosis marker | Type IV collagen (ng/ml) | ≥128 |

TABLE 2-2

| | | Cut-off values |
|---|---|---|
| Bile acid components | LCA (nmol/mL) | ≤0.0241 |
| | DCA (nmol/mL) | ≤0.175 |
| | SSBA (nmol/mL) | ≥21.1 |
| Oxidative stress marker | ROS (U) | ≥216 |
| Hepatic fibrosis markers | Type IV collagen (ng/ml) | ≥288 |
| | HA (ng/ml) | ≥47 |

A description is given of a specific example of the case where the test method according to the present invention is performed using specific cut-off values exemplified in Table 2-1 and Table 2-2 above.

A specific example of the test method according to the present invention may be a test method for discriminating a liver injury type, the test method including the steps of:

measuring a level of LCA in a serum sample collected from a subject;

comparing the measured level of LCA to a predetermined cut-off value of the level of LCA; and determining the liver injury type as hepatocellular injury type when the measured level of LCA is equal to or higher than a predetermined cut-off value of the level of LCA for identifying hepatocellular injury-type liver injury, in which the cut-off value is 0.0195 nmol/L.

In addition, another specific example of the test method may be a test method for discriminating a liver injury type, the test method including the steps of:

measuring a level of LCA in a serum sample collected from a subject;

comparing the measured level of LCA to a predetermined cut-off value of the level of LCA; and determining the liver injury type as cholestasis type when the measured level of LCA is equal to or lower than a predetermined cut-off value of the level of LCA for identifying hepatocellular injury-type liver injury, in which the cut-off value is 0.0241 nmol/L.

Still another specific example of the test method may be a test method for discriminating a liver injury type, the test method including the steps of:

measuring a level of LCA in a serum sample collected from a subject;

comparing the measured level of LCA to a predetermined cut-off value of the level of LCA; and determining the liver injury type as a mixed type of hepatocellular injury type and cholestasis type when the measured level of LCA is higher than a predetermined cut-off value of the level of LCA for identifying hepatocellular injury-type liver injury and is lower than a predetermined cut-off value of the level of LCA for identifying cholestasis-type liver injury, in which the predetermined cut-off value of the level of LCA for identifying hepatocellular injury-type liver injury is 0.0195 nmol/L and the predetermined cut-off value of the level of LCA for identifying cholestasis-type liver injury is 0.0241 nmol/L.

In addition, another specific example of the test method may be a test method for discriminating a liver injury type, the test method including the steps of:

measuring a level of LCA in a serum sample collected from a subject;

comparing the measured level of LCA to a predetermined cut-off value of the level of LCA;

further measuring any one or both of levels of UDCA and type IV collagen;

comparing the measured level of UDCA and/or type IV collagen to the predetermined cut-off value of the level of LCA UDCA and/or type IV collagen; and determining the liver injury type as hepatocellular injury type when the measured level of LCA is equal to or higher than a predetermined cut-off value of the level of LCA for identifying hepatocellular injury-type liver injury and the measured level of UDCA and/or type IV collagen satisfies any one of the following:

(1) the level of UDCA is equal to or lower than a predetermined cut-off value of the level of UDCA for identifying hepatocellular injury-type liver injury;

(2) the level of type IV collagen is equal to or higher than a predetermined cut-off value of the level of type IV collagen for identifying hepatocellular injury-type liver injury;

(3) the level of UDCA is equal to or lower than a predetermined cut-off value of the level of UDCA for identifying hepatocellular injury-type liver injury and the level of type IV collagen is equal to or higher than the predetermined cut-off value of the level of type IV collagen for identifying hepatocellular injury-type liver injury, in which the predetermined cut-off value of the level of LCA for identifying hepatocellular injury-type liver injury is 0.0195 nmol/L, the predetermined cut-off value of the level of UDCA for identifying hepatocellular injury-type liver injury is 0.903 nmol/L, and the predetermined cut-off value of the level of type IV collagen for identifying hepatocellular injury-type liver injury is 128 ng/ml.

In addition, another specific example of the test method may be a test method for discriminating a liver injury type, the test method including the steps of:

measuring a level of LCA in a serum sample collected from a subject;

comparing the measured level of LCA to a predetermined cut-off value of the level of LCA;

further measuring any one or more of levels of DCA, SSBA, type IV collagen, HA, and ROS, comparing each of the measured levels obtained by the further measurement to the corresponding predetermined cut-off value; and determining the liver injury type as cholestasis type when the measured level of LCA is equal to or lower than a predetermined cut-off value of the level of LCA for identifying cholestasis-type liver injury and the measured levels of DCA, SSBA, type IV collagen, HA, and ROS satisfy any one or two or more of the following:

(4) the level of DCA is equal to or lower than a predetermined cut-off value of the level of DCA for identifying cholestasis-type liver injury;

(5) the level of SSBA is equal to or higher than a predetermined cut-off value of the level of SSBA for identifying cholestasis-type liver injury;

(6) the level of type IV collagen is equal to or higher than a predetermined cut-off value of the level of type IV collagen for identifying cholestasis-type liver injury;

(7) the level of HA is equal to or higher than a predetermined cut-off value of the level of HA for identifying cholestasis-type liver injury; and (8) the level of ROS is equal to or higher than a predetermined cut-off value of the level of ROS for identifying cholestasis-type liver injury, in which: the predetermined cut-off value of the level of LCA for identifying cholestasis-type liver injury is 0.0241 nmol/L; the predetermined cut-off value of the level of DCA for identifying cholestasis-type liver injury is 0.175 nmol/L; the predetermined cut-off value of the level of SSBA for identifying cholestasis-type liver injury is 21.1 nmol/L; the predetermined cut-off value of the level of type IV collagen for identifying cholestasis-type liver injury is 288 ng/ml; the predetermined cut-off value of the level of HA for identifying cholestasis-type liver injury is 47 ng/ml; and the predetermined cut-off value of the level of ROS for identifying cholestasis-type liver injury is 216 U.

In addition, another specific example of the test method may be a test method for discriminating a liver injury type, the test method including the steps of:

measuring a level of LCA in a serum sample collected from a subject;

comparing the measured level of LCA to a predetermined cut-off value of the level of LCA;

further measuring a level of type IV collagen in the serum sample;

comparing the measured level of type IV collagen to a predetermined cut-off value of the level of type IV collagen; and determining the liver injury type as a mixed type of hepatocellular injury type and cholestasis type when the measured level of LCA is higher than a predetermined cut-off value of the level of LCA for identifying hepatocellular injury-type liver injury, and is lower than a predetermined cut-off value of the level of LCA for identifying cholestasis-type liver injury and when the measured level of type IV collagen is equal to or higher than a predetermined cut-off value of the level of type IV collagen for identifying cholestasis-type liver injury, in which: the predetermined cut-off value of the level of LCA for identifying hepatocellular injury-type liver injury and the predetermined cut-off value of the level of LCA for identifying cholestasis-type liver injury are 0.0195 nmol/L and 0.0241 nmol/L, respectively; and the predetermined cut-off value of the level of type IV collagen for identifying cholestasis-type liver injury is 288 ng/ml.

The measurement of levels of bile acid components may be performed by a method which has hitherto been used for the measurement. Examples thereof may include liquid chromatography-tandem mass spectrometry (LC-MS/MS) and gas chromatography-mass spectrometry (GC/MS). In addition, levels of bile acid or sulfated bile acid may be measured with a commercially available bile acid measurement kit. For example, the measurement of the level of sulfated bile acid may be performed with a UBASTEC-AUTO bile acid (USBA) kit (LBS Co., Ltd.). The measurement methods are not limited thereto and any method may be used for the measurement as long as the method can measure bile acids and components thereof.

The measurement of the level of type IV collagen may be performed by a method which has hitherto been used for the measurement. For example, the measurement of the level of type IV collagen may be performed with a commercially available type IV collagen measurement reagent kit. Examples of such method may include enzyme immunoassay (EIA) and enzyme-linked immunosorbent assay (ELISA) in which an antibody to type IV collagen is used. Specifically, a level of type IV collagen.7S may be measured as described below. Anti-human type IV collagen rabbit polyclonal antibody is added to a biological sample to produce a complex (complex 1) of type IV collagen.7S and anti-human type IV collagen rabbit polyclonal antibody, followed by adding with human type IV collagen.7S (labeled antigen) labeled with a radioisotope, such as iodine-125 ($^{125}$I), to form a complex (complex 2) with anti-human type IV collagen.7S rabbit polyclonal antibody which has failed to bind with type IV collagen.7S in the sample. Subsequently, anti-rabbit γ-globulin goat serum (goat antibody) is added to the complex 2, resulting in a reaction of the goat antibody with the complex 2 to form a complex of labeled antigen, anti-human type IV collagen.7S, and rabbit polyclonal antibody-goat antibody. The resultant precipitate is collected and its radioactivity is measured to determine the level of type IV collagen.7S.

The measurement of the level of HA may be performed by a method which has hitherto been used for the measurement. For example, the level of HA may be measured with a commercially available HA measurement reagent kit. An example of such method may be enzyme-linked immunosorbent assay (ELISA) in which an antibody to HA is used.

The measurement of the level of ROS may be performed by a method which has hitherto been used for the measurement. For example, the level of ROS may be measured with a commercially available ROS measurement reagent kit. Specifically, a total amount of substances producing free radicals may be measured as described below. Free radicals (ROO. or RO.) are generated from a peroxide (ROOH) by the Fenton reaction in which an ion of a metal, such as iron, is used as a catalyst, and the generated free radicals are allowed to react with N,N-diethyl-1,4-phenylene-diamine sulfate (abbreviated as DEPPD). Then, the DEPPD.+ generated by the reaction is subjected to measurement of absorbance at a wavelength of 505 nm.

The present invention encompasses a selection method of a therapeutic agent for liver injury according to a liver injury type, which is applied for a subject whose liver injury type is determined by the test method according to the present invention.

The present invention also encompasses a treatment method of liver injury according to a liver injury type, which is applied for a subject whose liver injury type is determined by the test method according to the present invention.

Examples of the therapeutic agent for liver injury and the treatment method of liver injury according to a liver injury type include therapeutic agents for liver injury and treatment method of liver injury which are described in "Manual for handling disorders due to adverse drug reactions, Drug-induced liver injury," and medications and treatment methods which are performed in medical facilities. In the case of the hepatocellular injury type, for example, intravenous injection of stronger Neo-Minophagen C formulation which is a glycyrrhizin formulation and has an anti-allergic action is performed as well as oral administration of UDCA. When hepatocellular injury is increased in severity to induce fulminant hepatitis, for example, intravenous hyperalimentation (IVH) or artificial liver support is used. In the case of the cholestasis type, for example, vitamin A or vitamin K is administered for covering lack of a liposoluble vitamin and then UDCA, prednisolone, phenobarbital, taurine, colestimide, or the like is used as a medication.

Now, the present invention is specifically described byway of Examples. However, the present invention is not construed as being limited to these Examples.

Example 1

In order to find a useful biomarker which enables early diagnosis of a liver injury type, serum samples obtained from liver injury patients and healthy volunteers were used to measure levels of bile acid components, and an oxidative stress marker and a hepatic fibrosis marker. The collection of serum samples and a serial experiment were performed after obtaining the consents of the sample donors, i.e. the patients and the healthy volunteers.

1. Subject Sample

Under the approval by the ethics committees of Daiichi Sankyo Co., Ltd. and the Jikei University School of Medicine, 304 serum samples were collected from 150 patients who were suspected of having liver injuries for about 2 years, such as viral, autoimmune, alcoholic, and genetic liver injuries. In addition, serum samples of healthy individuals obtained by blood collection from volunteers were used. The serum samples were stored at −80° C. until biomarkers were measured.

2. Evaluation Items

Levels of bile acid components, specifically, 24 kinds of bile acid components, i.e., CA, DCA, CDCA, UDCA, LCA, 12_KLCA, aMCA, PICA, HDCA, GCA, GDCA, GCDCA, GUDCA, GLCA, GHCA, GHDCA, TCA, TDCA, TCDCA, TUDCA, TLCA, TβMCA, THCA, and THDCA, and serum sulfated bile acid (SSBA) were measured.

In addition, levels of ALT, AST, ALP, γ-GTP, total bilirubin (hereinafter abbreviated as T.BIL), direct bilirubin (hereinafter abbreviated as D.BIL), TBA, and albumin (hereinafter abbreviated as ALB), and prothrombin time (hereinafter abbreviated as PT), which were biochemical parameters, were measured. Further, levels of 8-OHdG and ROS, which were oxidative stress markers, were measured as well as type IV collagen and HA, which were hepatic fibrosis markers.

3. Measurement Method

A total of 24 kinds of bile acid components were measured by a LC-MS/MS method. The minimum limit of determination was 0.03 nmol/ml only for 12-KLCA and 0.01 nmol/ml for other substances to be measured. The maximum limit of determination is 10 nmol/mL only for 12-KLCA and CA and 30 nmol/mL for other substances to be measured. Naptalam was used as an internal standard (IS). ACQUITY UPLC BEH C18 of 1.7 m and 2.1×50 mm (manufactured by Waters Corporation) was used for a column. 0.1% formic acid and acetonitrile were used for a mobile phase, the ratio of which was changed according to the measurement time. Electrospray ionization (abbreviated as ESI) negative was selected for ionization and selected ion recording (abbreviated as SIR) was selected for a detection method. Deproteinization was used as pretreatment. A level of sulfated bile acid was measured with BioMajesty JCA-BM2250 (JEOL Ltd.) using 300 µL of serum and a UBASTEC-AUTO bile acid (USBA) kit (LBS Co., Ltd.).

8-OHdG and ROS, which were oxidative stress markers, were measured as described below. 8-OHdG was measured with a reagent kit commercially available from Japan Institute for the Control of Aging. For measurement of ROS, free radicals (ROO. or RO.) are generated from a peroxide (ROOH) by the Fenton reaction in which an ion of a metal, such as iron, is used as a catalyst, and the generated free radicals were allowed to react with N,N-diethyl-1,4-phenylene-diamine sulfate (abbreviated as DEPPD). The DEPPD.+ generated by the reaction have an absorption at a wavelength of 505 nm. Then, the measurement of the absorbance was performed to determine a total amount of substances producing free radicals.

The biochemical parameters were measured by methods which were generally used in laboratory examinations.

Type IV collagen.7S and HA, which were hepatic fibrosis markers, were measured as described below. Type IV collagen.7S was allowed to react with anti-human type IV collagen rabbit polyclonal antibody to produce a type IV collagen.7S-anti-human type IV collagen rabbit polyclonal antibody complex (complex 1). Then, Iodine-125 ($^{125}$I)-labeled human type IV collagen.7S (labeled antigen) was added to react with anti-human type IV collagen.7S rabbit polyclonal antibody which had failed to bind with type IV collagen.7S in the sample, resulting in forming a labeled antigen-anti-human type IV collagen.7S rabbit polyclonal antibody complex (complex 2). Subsequently, anti-rabbit γ-globulin goat serum (goat antibody) was added to allow a reaction of the goat antibody with the complex 2, resulting in forming a complex of the labeled antigen, the anti-human type IV collagen.7S, and the rabbit polyclonal antibody-goat antibody as a precipitate. After an unreacted labeled antigen was removed, the radioactivity of the precipitate was measured and a level of type IV collagen.7S was determined. HA was measured with an HA ELISA kit (manufactured by Cosmo Bio Co., Ltd.).

4. Data Analysis Method

The correlation of variations in various biomarkers and liver injury symptoms comprehensively determined was analyzed. 304 serum samples obtained from 150 patients with liver injury were used and the summary statistics of the background information were calculated. The analysis was performed without taking the correlation between samples in the same case into account.

In order to investigate biomarkers associated with identification of types of liver injury based on symptoms, a multivariable logistic regression model adjusted by patient background factors was used to calculate the odds ratio for liver injury symptoms comprehensively determined by biomarker candidate factors (hepatocellular injury or cholestasis) with the 95% confidence interval. As the biomarker candidate factors, levels of bile acid components, oxidative stress markers, and hepatic fibrosis markers were used. Sex, age, EMI, alcohol drinking, therapeutic drugs for liver injury (antivirus agent, liver protection agent, bile acid formulation, amino acid formulation/hypoalbuminemia improving drug, and vitamin K formulation), and complications (dyslipidemia, diabetes, obstructive jaundice, and gallstone) were used as the patient background factors.

The presence or absence of liver injury symptoms was determined based on the assessment results given by two or more investigators adopted from the assessment results given by independent three investigators. Samples were used as a total analysis unit and the analysis was performed without taking the correlation between samples in the same case into account. A two-sided significance level of 5% was adopted when a statistical test was performed.

In the analysis of biomarkers, for indicators with no reference values, 97.5 percentiles of measured values of healthy individuals (corresponding to mean+2SD in the case of normal distribution) were set as reference values, and values higher than the reference values were categorized into high values and values lower than the reference values were categorized into low values.

Then, in order to determine objective assessment scales of biomarkers found to be associated with liver injury symptoms, serum samples of patients with no application of a therapeutic agent for liver injury were used to calculate cut-off values of the biomarkers which identify the presence or absence of liver injury symptoms. Though the calculation of a cut-off value may be performed by various procedures, the cut-off value was set to a value that derived through ROC analysis to maximize the sum of sensitivity and specificity.

5. Results

Background information on patients who have provided their serum samples is shown in Table 3.

TABLE 3

|  |  | Liver injury patients |
|---|---|---|
| Number of assessed samples |  | 304 |
| Sex | Male | 126 (41.4) |
|  | Female | 178 (58.6) |
| Age (years) | Mean (standard deviation) | 61.0 (15.2) |
|  | <65 | 160 (52.6) |
|  | >=65 | 144 (47.4) |
| BMI (kg/m$^2$) | Mean (standard deviation) | 23.6 (3.9) |
|  | <25 | 198 (65.1) |
|  | >=25 | 95 (31.3) |
|  | Impossible to calculate | 11 (3.6) |

TABLE 3-continued

|  |  |  | Liver injury patients |
| --- | --- | --- | --- |
| Alcohol drinking |  | No | 247 (81.3) |
|  |  | Yes | 50 (16.4) |
|  |  | Not known | 7 (2.3) |
| Theraputic drugs for liver injury Drugs usually (hitherto) taken | Antiviral agent (interferon) | Yes | 24 (7.9) |
|  | Liver protection drug (glycyrrhizin formulation etc.) | Yes | 44 (14.5) |
|  | Bile acid formulation (ursodeoxycholic acid) | Yes | 166 (54.6) |
|  | Amino acid formulation or hypoalbuminemia improving drug | Yes | 69 (22.7) |
|  | Bile acid adsorbent | Yes | 5 (1.6) |
|  | Vitamin K formulation | Yes | 51 (16.8) |
|  | Yubera N/EPL | Yes | 35 (11.5) |
|  | Herbal medicine (inchinkoto etc.) | Yes | 3 (1.0) |
|  | Others | Yes | 3 (1.0) |
| Other combined drugs Drugs usually (hitherto) taken | Therapeutic drug for hyperlipidemia (statin) | Yes | 21 (6.9) |
|  | Therapeutic drug for hyperlipidemia (ezetimibe) | Yes | 10 (3.3) |
|  | Therapeutic drug for hyperlipidemia (fiberate-based) | Yes | 3 (1.0) |
|  | Therapeutic drug for hyperlipidemia (tocopherol nicotinate/EPL) | Yes | 31 (10.2) |
|  | Depressor drug | Yes | 109 (35.9) |
|  | Therapeutic drug for diabetes | Yes | 33 (10.9) |
| Complications | Dyslipidemia | Yes | 57 (18.8) |
|  | Diabetes | Yes | 61 (20.1) |
|  | Obstructive jaundice | Yes | 12 (3.9) |
|  | Gallstone | Yes | 58 (19.1) |
|  | Others | Yes | 36 (11.8) |
| Biochemical parameters | ALT (U/L) | Median (interquartile range) | 56.0 (30.5, 92.5) |
|  | AST (U/L) | Median (interquartile range) | 55.0 (37.5, 99.5) |
|  | ALP (U/L) | Median (interquartile range) | 290.0 (231.0, 420.5) |
|  | γ-GTP (U/L) | Median (interquartile range) | 67.0 (32.0, 156.0) |
|  | T. BIL (mg/dl) | Median (interquartile range) | 1.1 (0.7, 1.7) |
|  | D. BIL (mg/dl) | Median (interquartile range) | 0.1 (0.1, 0.3) |
|  | TBA (μmol/L) | Median (interquartile range) | 18.0 (7.7, 42.3) |
|  | ALB (g/dl) | Median (interquartile range) | 3.7 (3.2, 4.1) |
|  | PT (%) | Median (interquartile range) | 84.0 (73.0, 96.0) |
| Levels of bile acid components | LCA (nmol/mL) | Median (interquartile range) | 0.0324 (0.0154, 0.0747) |
|  | 12_KLCA (nmol/mL) | Median (interquartile range) | 0.0393 (0.0199, 0.0832) |
|  | UDCA (nmol/mL) | Median (interquartile range) | 0.6915 (0.0721, 4.9150) |
|  | HDCA (nmol/mL) | Median (interquartile range) | 0.0000 (0.0000, 0.0055) |
|  | CDCA (nmol/mL) | Median (interquartile range) | 0.4340 (0.1070, 1.1700) |
|  | DCA (nmol/mL) | Median (interquartile range) | 0.2090 (0.0220, 0.7135) |
|  | αMCA (nmol/mL) | Median (interquartile range) | 0.0000 (0.0000, 0.0030) |
|  | βMCA (nmol/mL) | Median (interquartile range) | 0.0000 (0.0000, 0.0040) |
|  | CA (nmol/mL) | Median (interquartile range) | 0.1020 (0.0404, 0.3495) |
|  | GLCA (nmol/mL) | Median (interquartile range) | 0.0224 (0.0105, 0.0719) |
|  | GUDCA (nmol/mL) | Median (interquartile range) | 2.9600 (0.2165, 12.2000) |
|  | GHDCA (nmol/mL) | Median (interquartile range) | 0.0000 (0.0000, 0.0022) |
|  | GCDCA (nmol/mL) | Median (interquartile range) | 3.7000 (1.6100, 8.6450) |
|  | GDCA (nmol/mL) | Median (interquartile range) | 0.4890 (0.0366, 1.2650) |
|  | GHCA (nmol/mL) | Median (interquartile range) | 0.0442 (0.0213, 0.1125) |
|  | GCA (nmol/mL) | Median (interquartile range) | 0.9725 (0.4075, 3.0050) |
|  | TLCA (nmol/mL) | Median (interquartile range) | 0.0092 (0.0021, 0.0311) |
|  | TUDCA (nmol/mL) | Median (interquartile range) | 0.1520 (0.0165, 1.0800) |
|  | THDCA (nmol/mL) | Median (interquartile range) | 0.0000 (0.0000, 0.0001) |
|  | TCDCA (nmol/mL) | Median (interquartile range) | 0.7400 (0.2945, 2.9950) |
|  | TDCA (nmol/mL) | Median (interquartile range) | 0.0867 (0.0205, 0.2635) |
|  | TβMCA (nmol/mL) | Median (interquartile range) | 0.0013 (0.0000, 0.0482) |
|  | THCA (nmol/mL) | Median (interquartile range) | 0.0076 (0.0012, 0.0254) |
|  | TCA (nmol/mL) | Median (interquartile range) | 0.2435 (0.0648, 1.0300) |
|  | SSBA (nmol/mL) | Median (interquartile range) | 15.80 (8.78, 28.46) |
| Oxidative stress markers | 8-OHdG (ng/mL) | Median (interquartile range) | 0.16 (0.12, 0.22) |
|  | ROS (U) | Median (interquartile range) | 219.5 (182.5, 258.0) |
| Oxidative stress markers | Type IV collagen (ng/mL) | Median (interquartile range) | 186.5 (136.0, 258.0) |
|  | HA (ng/mL) | Median (interquartile range) | 136.0 (51.5, 388.0) |

Data are represented by the number of patients (%) or median (interquartile range).

Figure 3:
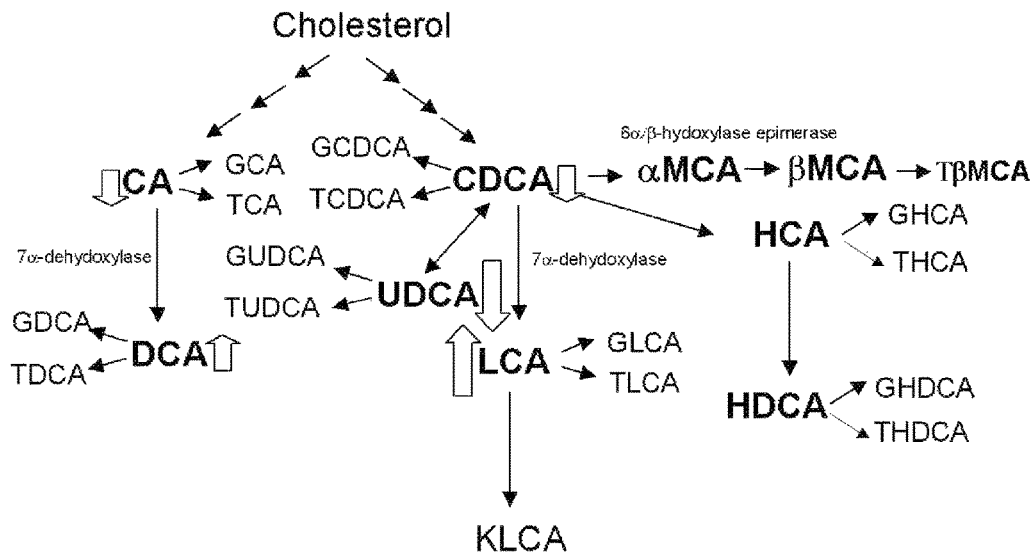
FIG. 3 is a schematic view for illustrating that in hepatocellular injury-type liver injury, the level of LCA showed a tendency to increase significantly and a level of UDCA showed a tendency to decrease significantly in bile acid components. Levels of CA and CDCA, which had an isomeric relationship with UDCA, tended to decrease with no significant difference and a level of DCA tended to increase with no significant difference.

Multivariable analysis with covariate adjustment was carried out for biomarkers which define symptoms of liver injury identified for types, and the results are shown in Table 4 and Table 5.

tionship with UDCA, and CA (OR=0.75, P=0.4702), which was also a primary bile acid, showed a tendency to be low, although their association with the hepatocellular injury type was weak (FIG. 3). When taurine conjugates and glycine

TABLE 4

| | | | Number of assessed samples | Hepatocellular injury type | | | Cholestasis type | | |
|---|---|---|---|---|---|---|---|---|---|
| | | | | Number of liver injury patient samples (%) | Odds ratio (95% confidence interval) | P value | Number of liver injury patient samples (%) | Odds ratio (95% confidence interval) | P value |
| Levels of bile acid components | LCA | <=97.5 pct | 144 | 90 (62.5) | 1.00 | — | 70 (48.6) | 1.00 | — |
| | | >97.5 pct | 160 | 125 (78.1) | 2.06 (1.16, 3.66) | 0.014 | 32 (20.0) | 0.29 (0.16, 0.53) | <0.0001 |
| | UDCA | <=97.5 pct | 148 | 109 (73.6) | 1.00 | — | 47 (31.8) | 1.00 | — |
| | | >97.5 pct | 156 | 106 (67.9) | 0.31 (0.12, 0.77) | 0.0112 | 55 (35.3) | 1.69 (0.71, 4.01) | 0.235 |
| | CDCA | <=97.5 pct | 268 | 194 (72.4) | 1.00 | — | 85 (31.7) | 1.00 | — |
| | | >97.5 pct | 36 | 21 (58.3) | 0.50 (0.22, 1.13) | 0.0950 | 17 (47.2) | 1.98 (0.88, 4.48) | 0.0991 |
| | DCA | <=97.5 pct | 232 | 160 (69.0) | 1.00 | — | 93 (40.1) | 1.00 | — |
| | | >97.5 pct | 72 | 55 (76.4) | 1.48 (0.74, 2.94) | 0.267 | 9 (12.5) | 0.26 (0.11, 0.58) | 0.001 |
| | CA | <=97.5 pct | 261 | 187 (71.6) | 1.00 | — | 85 (32.6) | 1.00 | — |
| | | >97.5 pct | 43 | 28 (65.1) | 0.75 (0.34, 1.65) | 0.470 | 17 (39.5) | 1.36 (0.63, 2.93) | 0.627 |
| | SSBA | <=97.5 pct | 201 | 137 (68.2) | 1.00 | — | 50 (24.9) | 1.00 | — |
| | | >97.5 pct | 103 | 78 (75.7) | 1.02 (0.49, 2.09) | 0.967 | 52 (50.5) | 5.05 (2.45, 10.41) | <0.0001 |
| Oxidative stress markers | 8-OHdG | <=97.5 pct | 292 | 210 (71.9) | 1.00 | — | 96 (32.9) | 1.00 | — |
| | | >97.5 pct | 12 | 5 (41.7) | 0.26 (0.07, 0.96) | 0.0434 | 6 (50.0) | 1.40 (0.35, 5.57) | 0.637 |
| | ROS | <=97.5 pct | 157 | 111 (70.7) | 1.00 | — | 36 (22.9) | 1.00 | — |
| | | >97.5 pct | 147 | 104 (70.7) | 0.84 (0.47, 1.52) | 0.570 | 66 (44.9) | 2.68 (1.49, 4.80) | 0.001 |
| Hepatic fibrosas markers | Type IV collagen | <=150 | 80 | 47 (58.8) | 1.00 | — | 20 (25.0) | 1.00 | — |
| | | >150 | 162 | 128 (79.0) | 2.19 (1.05, 4.56) | 0.036 | 62 (38.3) | 3.54 (1.62, 7.74) | 0.0015 |
| | HA | <=50 | 58 | 38 (65.5) | 1.00 | — | 13 (22.4) | 1.00 | — |
| | | >50 | 182 | 130 (71.4) | 1.20 (0.57, 2.56) | 0.629 | 70 (38.5) | 3.66 (1.28, 8.47) | 0.0024 |

Adjustment factors: sex, age, BMI, Alcohol drinking, therapeutic drugs for liver injury (antiviral agent, liver protection agent, bile acid formulation, amino acid formulation, hypoalbuminemia improving drug, and vitamin K formulation), and complications (dyslipidemia, diabetes, obstructive jaundica, and gallstone)

TABLE 5

| | | | Number of assessed samples | Hepatocellular injury type | | | Cholestasis type | | |
|---|---|---|---|---|---|---|---|---|---|
| | | | | Number of liver injury patient samples (%) | Odds ratio (95% confidence interval) | P value | Number of liver injury patient samples (%) | Odds ratio (95% confidence interval) | P value |
| Levels of bile acid components | 12_KLCA | <=97.5 pct | 235 | 165 (70.2) | 1.00 | — | 77 (32.8) | 1.00 | — |
| | | >97.5 pct | 69 | 50 (72.5) | 0.88 (0.45, 1.71) | 0.70 | 25 (36.2) | 1.03 (0.53, 1.98) | 0.939 |
| | GLCA | <=97.5 pct | 182 | 113 (62.1) | 1.00 | — | 74 (40.7) | 1.00 | — |
| | | >97.5 pct | 122 | 102 (83.6) | 2.17 (1.13, 4.15) | 0.0195 | 28 (23.0) | 0.56 (0.30, 1.04) | 0.0655 |
| | GUDCA | <=97.5 pct | 140 | 104 (74.3) | 1.00 | — | 45 (32.1) | 1.00 | — |
| | | >97.5 pct | 164 | 111 (67.7) | 0.16 (0.05, 0.47) | 0.0009 | 57 (34.8) | 2.08 (0.78, 5.55) | 0.143 |
| | GCDCA | <=97.5 pct | 168 | 114 (67.9) | 1.00 | — | 36 (21.4) | 1.00 | — |
| | | >97.5 pct | 136 | 101 (74.3) | 1.29 (0.69, 2.42) | 0.430 | 66 (48.5) | 4.25 (2.23, 8.10) | <0.0001 |
| | GDCA | <=97.5 pct | 255 | 169 (66.3) | 1.00 | — | 94 (36.9) | 1.00 | — |
| | | >97.5 pct | 49 | 46 (93.9) | 7.34 (2.11, 25.53) | 0.0017 | 8 (16.3) | 0.35 (0.15, 0.84) | 0.0182 |
| | GCA | <=97.5 pct | 220 | 154 (70.0) | 1.00 | — | 50 (22.7) | 1.00 | — |
| | | >97.5 pct | 84 | 61 (72.6) | 1.09 (0.54, 2.16) | 0.824 | 52 (61.9) | 6.11 (3.06, 12.23) | <0.0001 |
| | TLCA | <=97.5 pct | 209 | 132 (63.2) | 1.00 | — | 68 (32.5) | 1.00 | — |
| | | >97.5 pct | 95 | 83 (87.4) | 4.68 (2.01, 10.88) | 0.0003 | 34 (35.8) | 1.15 (0.59, 2.24) | 0.678 |
| | TUDCA | <=97.5 pct | 152 | 105 (69.1) | 1.00 | — | 46 (30.3) | 1.00 | — |
| | | >97.5 pct | 152 | 110 (72.4) | 0.56 (0.22, 1.42) | 0.221 | 56 (36.8) | 3.20 (1.18, 8.64) | 0.0221 |
| | TCDCA | <=97.5 pct | 175 | 113 (64.6) | 1.00 | — | 41 (23.4) | 1.00 | — |
| | | >97.5 pct | 129 | 102 (79.1) | 2.31 (1.17, 4.54) | 0.0152 | 61 (47.3) | 3.32 (1.76, 6.29) | 0.0002 |
| | TDCA | <=97.5 pct | 256 | 172 (67.2) | 1.00 | — | 83 (34.4) | 1.00 | — |
| | | >97.5 pct | 48 | 43 (89.6) | 3.60 (1.31, 9.89) | 0.0131 | 14 (29.2) | 0.85 (0.39, 1.83) | 0.675 |
| | TCA | <=97.5 pct | 222 | 154 (69.4) | 1.00 | — | 52 (23.4) | 1.00 | — |
| | | >97.5 pct | 82 | 61 (74.4) | 1.17 (0.57, 2.40) | 0.670 | 50 (61.0) | 7.54 (3.65, 15.60) | <0.0001 |

Adjustment factors: sex, age, BMI, alcohol drinking, therapeutic drugs for liver injury (antiviral agent, liver protection agent, bile acid formulation, amino acid formulation, hypoalbuminemia improving drug, and vitamin K formulation), and complications (dyslipidemia, diabetes, obstructive jaundice, and gallstone)

Factors found to be significantly associated with the hepatocellular injury type are LCA (OR=2.06, P=0.0140), UDCA (OR=0.31, P=0.0112), and type IV collagen (OR=2.19, P=0.0357). The levels of LCA and type IV collagen showed a tendency to be high and the level of UDCA showed a tendency to be low (Table 4). The levels of CDCA (OR=0.50, P=0.0950), which had an isomeric relaconjugates of bile acids were taken into consideration, the levels of TCDCA (OR-2.31, P=0.0152), GDCA (OR=7.34, P=0.0017), TDCA (OR-3.60, P=0.0131), GLCA (OR=2.17, P=0.0195), and TLCA (OR=4.68, P=0.0003) showed a tendency to be significantly high and the level of GUDCA (OR=0.16, P=0.0009) showed a tendency to be significantly low.

Figure 4:
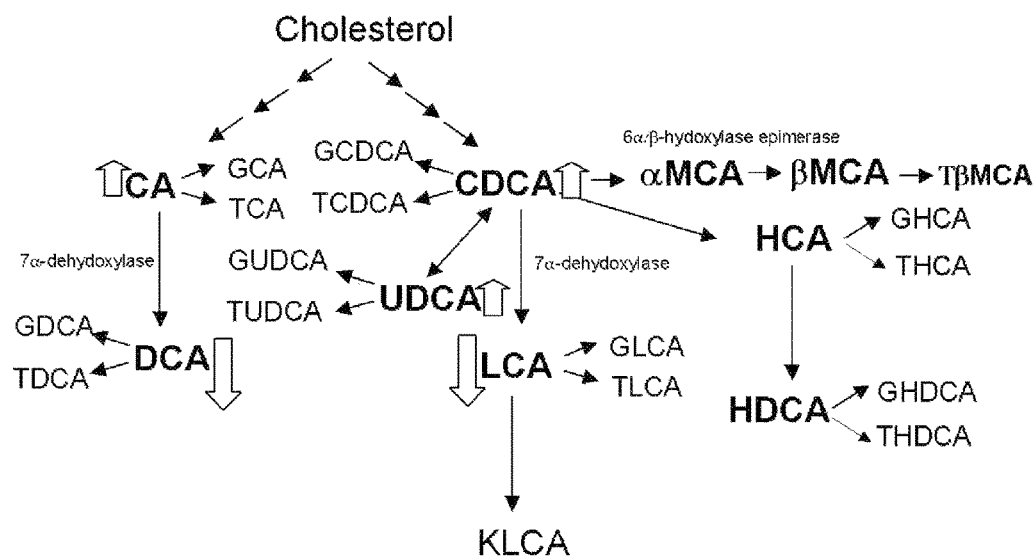
FIG. 4 is a schematic view for illustrating that in cholestasis-type liver injury, both of the levels of LCA and DCA showed a tendency to increase significantly in bile acid components. All of the levels of CDCA, UDCA, and CA showed a tendency to decrease with no significant difference.

Meanwhile, factors found to be significantly associated with the cholestasis type are LCA (OR=0.29, P<0.0001), DCA (OR=0.26, P=0.0010), SSBA (OR=5.05, P<0.0001), type IV collagen (OR=3.54, P=0.0015), HA (OR=3.66, P=0.0024), and ROS (OR=2.68, P=0.0010). The levels of LCA and DCA showed a tendency to be low and the levels of other factors than LCA and DCA showed a tendency to be high (Table 4). Meanwhile, it was found that the levels of CDCA (OR=1.98, P=0.0991), UDCA (OR=1.69, P=0.2353), and CA (OR=1.36, P=0.4269) showed a tendency to be high, although their association with the cholestasis type was weak. That is, contrasting results to the hepatocellular injury type were shown (FIG. 4). When taurine conjugates and glycine conjugates of bile acids were taken into consideration, the levels of GCDCA (OR=4.25, P<0.0001), TCDCA (OR=3.32, P=0.0002), GCA (OR=6.11, P<0.0001), TCA (OR=7.54, P<0.0001), and TUDCA (OR=3.20, P=0.0221) showed a tendency to be significantly high and the level of GDCA (OR=0.35, P=0.0182) showed a tendency to be low. It was found that the level of type IV collagen, which was an indicator of hepatic fibrosis, also showed a tendency to be high in the cholestasis type similarly to the hepatocellular injury type.

In the biomarkers found to be associated with liver injury symptoms, cut-off values which can be used as references for determination of a liver injury type are calculated from serum samples of patients with no application of a therapeutic drug for liver injury, and the results are shown in Table 2-1 and Table 2-2. Cut-off values of biomarkers for identifying hepatocellular injury-type liver injury are shown in Table 2-1. Cut-off values of biomarkers for identifying cholestasis-type liver injury are shown in Table 2-2.

When comparing the results of the multivariable analysis between the hepatocellular injury type and the cholestasis type, it was found that LCA increased in the hepatocellular injury type, and in contrast, decreased in the cholestasis type. From the results, it was suggested that LCA was a useful marker for discrimination of liver injury symptoms. It can be considered that in the hepatocellular injury type, LCA, which was a secondary bile acid, showed a high value. With this increased metabolism, UDCA, which is an isomer of CDCA that is a parent compound of LCA, showed a low value. Meanwhile, it can be considered that in the cholestasis type, CDCA and CA, which were primary bile acids, showed a tendency to increase owing to cholestasis, although their association with the cholestasis type was weak. With this increased level, excretion of bile acids to intestinal tract was suppressed, resulting in decreased levels of DCA and LCA. In addition, in the hepatocellular injury type, TCDCA, GDCA, TDCA, GLCA, and TLCA significantly increased, while GUDCA significantly decreased, which may be considered as below. With a significant increase in LCA and a change in DCA found to show a tendency to increase but without significance, production of conjugates thereof was also enhanced. GUDCA showed a tendency to decrease with a decrease in UDCA, but TCDCA, which was a taurine conjugate of CDCA, show a tendency to increase. From the results, it was suggested that in the hepatocellular injury type, metabolism from a primary bile acid to a secondary bile acid having high lipid-solubility was increased. It was found that in the cholestasis type, GCDCA, TCDCA, GCA, TCA, and TUDCA significantly increased, while GDCA decreased. From the results, it can be considered that both conjugated reactions of CDCA and CA was increased due to cholestasis. It has been reported that SSBA increases in biliary diseases (Non Patent Literature 12). Also in this test, SSBA showed a high value in the cholestasis type, but no significant change in SSBA was found in the hepatocellular injury type.

It was found that the measured hepatic fibrosis markers significantly increased in both the hepatocellular injury type and the cholestasis type. Among the measured oxidative stress markers, 8-OHdG tended to significantly decrease in the hepatocellular injury type, but the value was not largely changed compared to that of a healthy population. The number of samples of the patient population having a level of 8-OHdG higher than the cut-off value was small. Thus, the association of 8-OHdG with the hepatocellular injury type could not be clearly determined. In addition, ROS, which was reactive oxygen, showed a high value in the cholestasis type, but no significant change in ROS was found in the hepatocellular injury type.

Biochemical parameters, which have hitherto been used in examination of liver diseases, have low correlations with the biomarkers measured in this examination, and hence, it is difficult to accurately discriminate liver injury symptoms with only use of these biochemical parameters.

From those results, it was suggested that the level of LCA was specific for each of the hepatocellular injury type and the cholestasis type and showed significant changes, and hence was useful as a marker for discriminating types of liver injury symptoms. In addition, primary bile acids and SSBA are also effective for determination of hepatocellular injury type, cholestasis type, and a mixed type thereof as markers which may assist discrimination of types of liver injury symptoms using the level of LCA.

INDUSTRIAL APPLICABILITY

As described above, the present invention provides a test method for discriminating a liver injury type. The present invention enables early diagnosis and early determination of a therapeutic strategy of a liver injury type based on clinical symptoms, specifically, hepatocellular injury type, cholestasis type, and a mixed type thereof. As described above, the present invention is extremely useful in the field of examination of liver diseases.

The invention claimed is:
1. A method for treating a liver injury, comprising:
measuring a level of lithocholic acid (LCA), in a serum sample collected from a human subject; and
identifying the liver injury as hepatocellular injury, cholestasis, or mixed type injury comprising hepatocellular injury and cholestasis, based on the measured level of LCA,
wherein the liver injury is identified as hepatocellular injury when the measured level of LCA is equal to or higher than a first predetermined cut-off value of the level of LCA for identifying hepatocellular injury,
wherein the liver injury is identified as cholestasis when the measured level of LCA is equal to or lower than a second predetermined cut-off value of the level of LCA for identifying cholestasis,
wherein the liver injury is identified as mixed type of hepatocellular injury and cholestasis when the measured level of LCA is higher than the first predetermined cut-off value of the level of LCA for identifying hepatocellular injury and is lower than the second predetermined cut-off value of the level of LCA for identifying cholestasis; and
performing a suitable treatment on the human subject wherein the suitable treatment comprises an intravenous injection of a Stronger Neo-Minophagen C formulation, an intravenous injection of a glycyrrhizin formulation, an intravenous hyperalimentation (IVH), or artificial liver support, or any combination thereof for hepatocellular injury, and comprises administration of vitamin A, vitamin K, UDCA, prednisolone, phenobarbital, taurine, or colestimide, or any combination thereof for cholestasis, and comprises a suitable treatment for hepatocellular injury, cholestasis, or both for a mixed type injury.

2. The method according to claim 1, wherein the measuring further comprises:
measuring any one or both of levels of ursodeoxycholic acid (UDCA), and type IV collagen; and
the liver injury is identified as hepatocellular injury when the measured level of LCA is equal to or higher than the first predetermined cut-off value of the level of LCA for identifying hepatocellular injury and the measured level of UDCA and/or type IV collagen satisfies any one of the following:
(1) the level of UDCA is equal to or lower than a predetermined cut-off value of the level of UDCA for identifying hepatocellular injury;
(2) the level of type IV collagen is equal to or higher than a predetermined cut-off value of the level of type IV collagen for identifying hepatocellular injury; and
(3) the level of UDCA is equal to or lower than a predetermined cut-off value of the level of UDCA for identifying hepatocellular injury and the level of type W collagen is equal to or higher than a predetermined cut-off value of the level of type IV collagen for identifying hepatocellular injury.

3. The method according to claim 1, wherein the measuring further comprises:
measuring any one or more of levels of deoxycholic acid (DCA), serum sulfated bile acid (SSBA), type IV collagen, hyaluronic acid (HA), and reactive oxygen species (ROS); and
the liver injury is identified as cholestasis when the measured level of LCA is equal to or lower than the second predetermined cut-off value of the level of LCA for identifying cholestasis and the measured levels of DCA, SSBA, type IV collagen, HA, and ROS satisfy any one or two or more of the following:
(1) the level of DCA is equal to or lower than a predetermined cut-off value of the level of DCA for identifying cholestasis;
(2) the level of SSBA is equal to or higher than a predetermined cut-off value of the level of SSBA for identifying cholestasis;
(3) the level of type IV collagen is equal to or higher than a predetermined cut-off value of the level of type IV collagen for identifying cholestasis;
(4) the level of HA is equal to or higher than a predetermined cut-off value of the level of HA for identifying cholestasis; and
(5) the level of ROS is equal to or higher than a predetermined cut-off value of the level of ROS for identifying cholestasis.

4. The method according to claim 1, wherein the measuring further comprises:
measuring a level of type IV collagen; and
the liver injury is identified as mixed type of hepatocellular injury and cholestasis when the measured level of LCA is higher than the first predetermined cut-off value of the level of LCA for identifying hepatocellular injury and is lower than the second predetermined cut-off value of the level of LCA for identifying cholestasis and when the measured level of type IV collagen is equal to or higher than a predetermined cut-off value of the level of type IV collagen for identifying cholestasis.

5. The method according to claim 1, wherein the first predetermined cut-off value of the level of LCA for identifying hepatocellular injury is calculated from a predetermined receiver operating characteristic (ROC) curve of the level of LCA for hepatocellular injury.

6. The method according to claim 1, wherein the second predetermined cut-off value of the level of LCA for identifying cholestasis is calculated from a predetermined ROC curve of the level of LCA for cholestasis.

7. The method according to claim 2, wherein the first predetermined cut-off value of the level of LCA for identifying hepatocellular injury, the predetermined cut-off value of the level of UDCA for identifying hepatocellular injury, and the predetermined cut-off value of the level of type IV collagen for identifying hepatocellular injury are calculated from a predetermined ROC curve of the level of LCA for hepatocellular injury, a predetermined ROC curve of the level of UDCA for hepatocellular injury, and a predetermined ROC curve of the level of type IV collagen for hepatocellular disease, respectively.

8. The method according to claim 3, wherein the second predetermined cut-off value of the level of LCA for identifying cholestasis, the predetermined cut-off value of the level of DCA for identifying cholestasis, the predetermined cut-off value of the level of SSBA for identifying cholestasis, the predetermined cut-off value of the level of type IV collagen for identifying cholestasis, the predetermined cut-off value of the level of HA for identifying cholestasis, and the predetermined cut-off value of the level of ROS for identifying cholestasis are calculated from a predetermined ROC curve of the level of LCA for cholestasis, a predetermined ROC curve of the level of DCA for cholestasis, a predetermined ROC curve of the level of SSBA for cholestasis, a predetermined ROC curve of the level of type IV collagen for cholestasis, a predetermined ROC curve of the level of HA for cholestasis, and a predetermined ROC curve of the level of ROS for cholestasis, respectively.

9. The method according to claim 1, further comprising selecting a therapeutic agent suitable for treating the identified liver injury after the identifying and before the performing of the treatment using the selected therapeutic agent.

10. A method for treating a liver injury, comprising:
identifying the liver injury as hepatocellular injury, cholestasis, or mixed type injury comprising hepatocellular injury and cholestasis, based on a measured level of lithocholic acid (LCA) in a serum sample collected from a human subject,
wherein the liver injury is identified as hepatocellular injury when the measured level of LCA is equal to or higher than a first predetermined cut-off value of the level of LCA for identifying hepatocellular injury,
wherein the liver injury is identified as cholestasis when the measured level of LCA is equal to or lower than a second predetermined cut-off value of the level of LCA for identifying cholestasis,
wherein the liver injury is identified as mixed type of hepatocellular injury and cholestasis when the measured level of LCA is higher than the first predetermined cut-off value of the level of LCA for identifying hepatocellular injury and is lower than the second predetermined cut-off value of the level of LCA for identifying cholestasis; and
performing a suitable treatment on the human subject wherein the suitable treatment comprises an intravenous injection of a Stronger Neo-Minophagen C formulation, an intravenous injection of a glycyrrhizin formulation, an intravenous hyperalimentation (IVH), or artificial liver support, or any combination thereof for hepatocellular injury, and comprises administration of vitamin A, vitamin K, UDCA, prednisolone, phenobarbital, taurine, or colestimide, or any combination thereof for cholestasis, and comprises a suitable treatment for hepatocellular injury, cholestasis, or both for a mixed type injury.

11. The method according to claim 10, wherein the identifying comprises comparing the measured level of LCA to the first and second predetermined cut-off values of the level of LCA.

12. The method according to claim 10, wherein the measuring further comprises:
    measuring any one or both of levels of ursodeoxycholic acid (UDCA), and type IV collagen; and
    the liver injury is identified as hepatocellular injury when the measured level of LCA is equal to or higher than the first predetermined cut-off value of the level of LCA for identifying hepatocellular injury and the measured level of UDCA and/or type IV collagen satisfies any one of the following:
    (1) the level of UDCA is equal to or lower than a predetermined cut-off value of the level of UDCA for identifying hepatocellular injury;
    (2) the level of type IV collagen is equal to or higher than a predetermined cut-off value of the level of type IV collagen for identifying hepatocellular injury; and
    (3) the level of UDCA is equal to or lower than a predetermined cut-off value of the level of UDCA for identifying hepatocellular injury and the level of type IV collagen is equal to or higher than a predetermined cut-off value of the level of type IV collagen for identifying hepatocellular injury.

13. The method according to claim 10, wherein the measuring further comprises:
    measuring any one or more of levels of deoxycholic acid (DCA), serum sulfated bile acid (SSBA), type IV collagen, hyaluronic acid (HA), and reactive oxygen species (ROS); and
    the liver injury is identified as cholestasis when the measured level of LCA is equal to or lower than the second predetermined cut-off value of the level of LCA for identifying cholestasis and the measured levels of DCA, SSBA, type IV collagen, HA, and ROS satisfy any one or two or more of the following:
    (1) the level of DCA is equal to or lower than a predetermined cut-off value of the level of DCA for identifying cholestasis;
    (2) the level of SSBA is equal to or higher than a predetermined cut-off value of the level of SSBA for identifying cholestasis;
    (3) the level of type IV collagen is equal to or higher than a predetermined cut-off value of the level of type IV collagen for identifying cholestasis;
    (4) the level of HA is equal to or higher than a predetermined cut-off value of the level of HA for identifying cholestasis; and
    (5) the level of ROS is equal to or higher than a predetermined cut-off value of the level of ROS for identifying cholestasis.

14. The method according to claim 10, wherein the measuring further comprises:
    measuring a level of type IV collagen; and
    the liver injury is identified as mixed type of hepatocellular injury and cholestasis when the measured level of LCA is higher than the first predetermined cut-off value of the level of LCA for identifying hepatocellular injury and is lower than the second predetermined cut-off value of the level of LCA for identifying cholestasis and when the measured level of type IV collagen is equal to or higher than a predetermined cut-off value of the level of type IV collagen for identifying cholestasis.

15. The method according to claim 10, wherein the first predetermined cut-off value of the level of LCA for identifying hepatocellular injury is calculated from a predetermined ROC curve of the level of LCA for hepatocellular injury.

16. The method according to claim 10, wherein the second predetermined cut-off value of the level of LCA for identifying cholestasis is calculated from a predetermined ROC curve of the level of LCA for cholestasis.

17. The method according to claim 12, wherein the first predetermined cut-off value of the level of LCA for identifying hepatocellular injury, the predetermined cut-off value of the level of UDCA for identifying hepatocellular injury, and the predetermined cut-off value of the level of type IV collagen for identifying hepatocellular injury are calculated from a predetermined ROC curve of the level of LCA for hepatocellular injury, a predetermined ROC curve of the level of UDCA for hepatocellular injury, and a predetermined ROC curve of the level of type IV collagen for hepatocellular disease, respectively.

18. The method according to claim 13, wherein the second predetermined cut-off value of the level of LCA for identifying cholestasis, the predetermined cut-off value of the level of DCA for identifying cholestasis, the predetermined cut-off value of the level of SSBA for identifying cholestasis, the predetermined cut-off value of the level of type IV collagen for identifying cholestasis, the predetermined cut-off value of the level of HA for identifying cholestasis, and the predetermined cut-off value of the level of ROS for identifying cholestasis are calculated from a predetermined ROC curve of the level of LCA for cholestasis, a predetermined ROC curve of the level of DCA for cholestasis, a predetermined ROC curve of the level of SSBA for cholestasis, a predetermined ROC curve of the level of type IV collagen for cholestasis, a predetermined ROC curve of the level of HA for cholestasis, and a predetermined ROC curve of the level of ROS for cholestasis, respectively.

19. The method according to claim 10, further comprising selecting a therapeutic agent suitable for treating the identified liver injury after the identifying and before the performing of the treatment using the selected therapeutic agent.

* * * * *